United States Patent [19]

Miller et al.

[11] Patent Number: 5,041,547
[45] Date of Patent: Aug. 20, 1991

[54] CHROMOGENIC SUBSTITUTED 4,7-DIAZAPHTHALIDES

[75] Inventors: Robert E. Miller; Troy E. Hoover, both of Hoover, Wis.

[73] Assignee: Appleton Papers Inc., Appleton, Wis.

[21] Appl. No.: 542,286

[22] Filed: Jun. 22, 1990

Related U.S. Application Data

[63] Continuation of Ser. No. 901,108, Aug. 28, 1986, abandoned.

[51] Int. Cl.$^5$ .............. C07D 491/048; C07D 403/06; B41M 5/12; C09B 11/26
[52] U.S. Cl. ........................... 544/350; 544/405
[58] Field of Search ......................... 544/350

[56] References Cited

U.S. PATENT DOCUMENTS 3,853,869 12/1974 Farker ................. 544/350
4,016,174 4/1977 Farker ................. 544/350

FOREIGN PATENT DOCUMENTS 54277 6/1982 European Pat. Off. .
48-3204 1/1973 Japan ................. 544/350
48-3205 1/1973 Japan ................. 544/350

OTHER PUBLICATIONS

Akamatsu Chem Abs 83, 50814(1974).

*Primary Examiner*—Mark L. Berch
*Attorney, Agent, or Firm*—Paul S. Phillips, Jr.; Benjamin Mieliulis

[57] ABSTRACT

The invention relates to novel substituted 4,7-diazaphthalides of the general formula

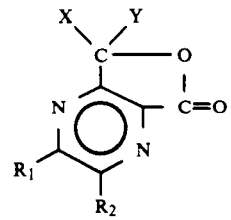

wherein X and Y each independently of the other, are optionally substituted aminophenyl, indolyl, benzoindolyl, jujolidinyl or kairolyl radicals; and $R_1$ and $R_2$, each independently of the other, are hydrogen, lower alkyl or optionally substituted phenyl, provided that both $R_1$ and $R_2$ are not hydrogen.

These compounds are particularly suitable for use as color formers in pressure-sensitive or heat-sensitive recording materials.

8 Claims, No Drawings

CHROMOGENIC SUBSTITUTED 4,7-DIAZAPHTHALIDES

This application is a continuation of Ser. No. 06/901,108, filed Aug. 28, 1986 now abandoned.

The present invention relates to chromogenic substituted 4,7-diazaphthalides, to the preparation thereof and to the use thereof as color formers in pressure-sensitive or heat-sensitive recording materials. The substituted 4,7-diazaphthalides have the general formula

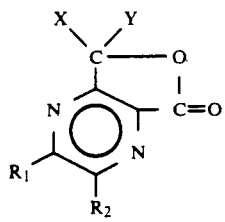

wherein X and Y, each independently of the other, are optionally substituted aminophenyl, indolyl, benzoindolyl, julolidinyl or kairolyl
$R_1$ and $R_2$, each independently of the other, are hydrogen, lower alkyl or optionally substituted phenyl, provided that both $R_1$ and $R_2$ are U.S. Pat. Nos. 3,775,424 and 3,853,869 and Japanese Publication Nos. 48-3204 and 48-3205 describe 4,7-diazaphthalide compounds.

Colorable novel chromogenic substituted 4,7-diazaphthalide compounds have been discovered. These compounds are initially substantially colorless but produce colored products on reaction with certain acidic developer materials. It is an object of this invention to provide such substituted 4,7-diazaphrhalide compounds, methods for making them and mark-forming record systems containing them.

It is another object of this invention to provide chromogenic compounds which are substantially unreactive to base paper.

It is yet another object of this invention to provide chromogenic compounds which produce substantially no premature coloration during the process of microencapsulating a composition containing said chromogenic compound.

It is still another object of this invention to provide chromogenic compounds which possess an improved lightfastness of their colored form U.S. Pat. Nos. 3,775,424 and 3,853,869, which are hereby incorporated by reference, disclose certain 4,7-diazaphthalide (pyrazine) compounds which have utility as color formers in pressure-sensitive and heat sensitive recording systems. These compounds do, however, have the disadvantage that they are too sensitive in their color-forming function. This excess sensitivity of the compounds results in inadvertent coloration when the compounds come in contact with the base paper upon which pressure sensitive or heat-sensitive compositions are coated. The excess sensitivity also results in premature coloration when a composition containing the compound is microencapsulated. The compounds of the present invention, surprisingly, have the ability to produce intense coloration when brought into contact with acidic developer materials but produce substantially no color when a composition containing same is microencapsulated or is brought into contact with paper base stock.

Important groups of colorable chromogenic compounds of the present invention may be defined by the formula

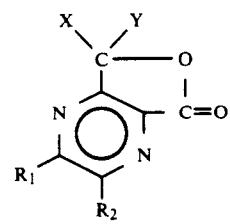

wherein X and Y, each independently of the other, are optionally substituted aminophenyl, indolyl, benzoindolyl, julolidinyl or kairolyl radicals; and
$R_1$ and $R_2$, each independently of the other, are hydrogen, lower alkyl of optionally substituted phenyl, provided that both $R_1$ and $R_2$ are not hydrogen.

Among the more important compounds of this invention are the ones defined by the formula

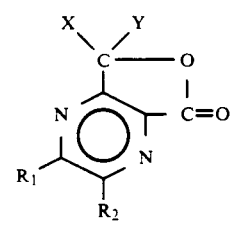

wherein X and Y, each independently of the other, are

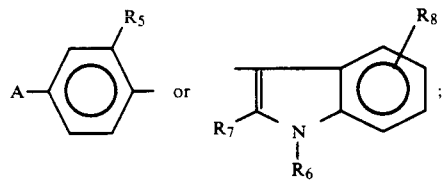

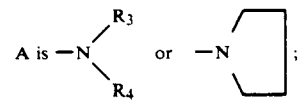

$R_1$ and $R_2$, each independently of the other, are hydrogen, lower alkyl or phenyl provided that both $R_1$ and $R_2$ are not hydrogen;

$R_3$ and $R_4$, each independently of the other, are $C_1$–$C_8$ alkyl cyclohexyl, phenyl or phenyl substituted by lower alkyl or lower alkoxy;

$R_5$ is hydrogen or $C_1$–$C_8$ alkoxy;

$R_6$ is $C_1$–$C_8$ alkyl or cyclohexyl;

$R_7$ is lower alkyl; and $R_8$ is hydrogen or lower alkyl,

In the context of the present invention lower alkyl are those alkyl groups containing one through four carbon atoms and lower alkoxy are those alkoxy groups containing one through four carbon atoms.

The more preferred among the compounds of this invention are the ones represented by the following formula

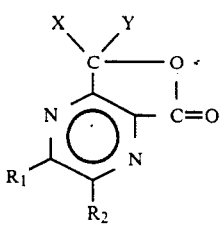

wherein X and Y, each independently of the other, are

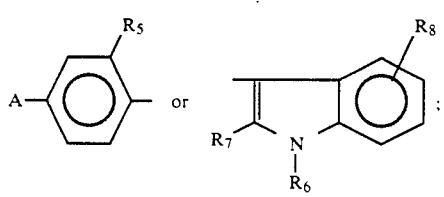

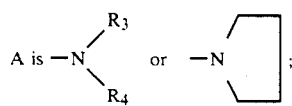

$R_1$ and $R_2$ each independently of the other, are hydrogen, lower alkyl, provided that both $R_1$ and $R_2$ are not hydrogen;

$R_3$ and $R_4$, each independently of the other, are $C_1$-$C_8$ alkyl cyclohexyl, phenyl or phenyl substituted by lower alkyl or lower alkoxy;

$R_5$ is hydrogen or lower alkoxy;

$R_6$ is $C_1$-$C_8$ alkyl;

$R_7$ is lower alkyl; and $R_8$ is hydrogen or lower alkyl.

Most preferred among the compounds of this invention are those represented by the formula

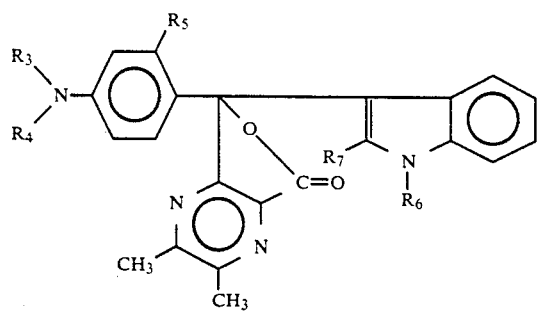

wherein $R_3$ and $R_4$ each independently of the other are $C_1$-$C_8$ alkyl, cyclohexyl, phenyl, or phenyl substituted by lower alkyl or lower alkoxy:

$R_5$ is lower alkoxy;

$R_6$ is $C_1$-$C_8$ alkyl; and $R_7$ is lower alkyl.

One process for the preparation of the compounds of the present invention, hereinafter referred to as process I, consists of the following series of reaction wherein $R_1$, $R_2$, $R_3$, $R_4$, $R_5$, $R_6$, $R_7$ and $R_8$ have the given meanings.

The first step consists of oxidizing substituted quinoxaline to substituted pyrazine-2,3-dicarboxylic acid according to the following process.

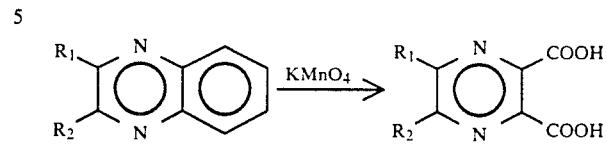

The resulting dicarboxylic acid is converted to the anhydride by heating with acetic anhydride.

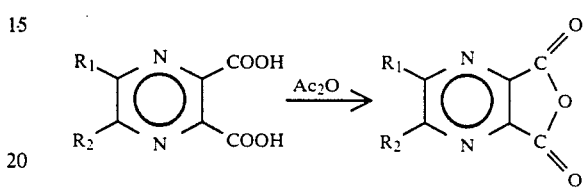

The resulting anhydride can then be condensed with an indole to give a keto-acid intermediate

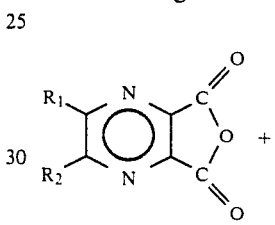

+

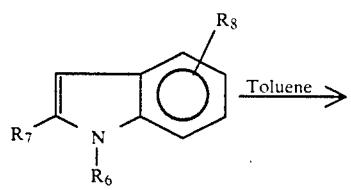

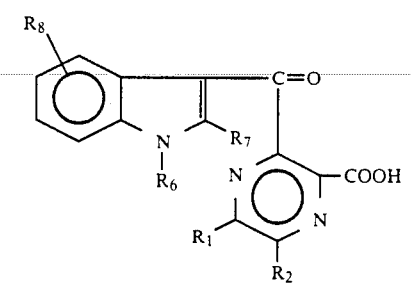

The final chromogenic compound is then obtained by condensation of the keto-acid with the appropriate amine.

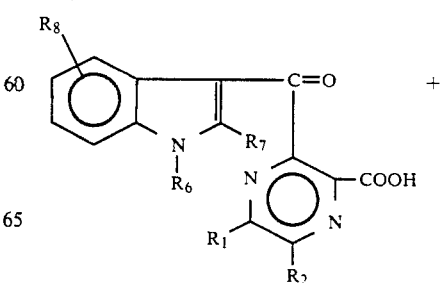

+

-continued

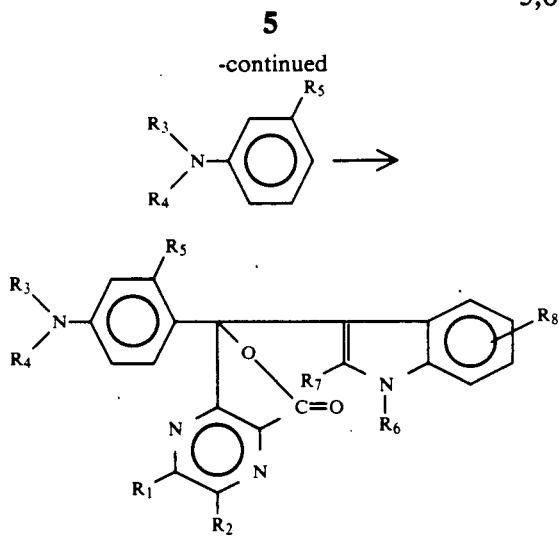

The preceding steps have exemplified the process to make

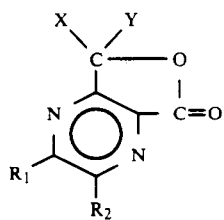

wherein X is an optionally substituted aminophenyl radical and Y is an optionally substituted indolyl radical.

The process in its broadest sense involves condensing the anhydride with the appropriate X compound to produce the keto-acid intermediate

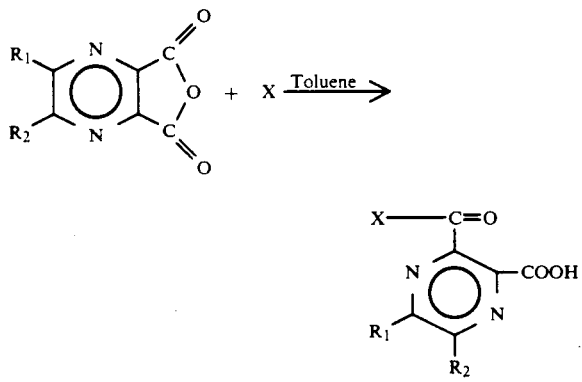

which is the condensed with the appropriate Y compound to form the final chromogenic compound

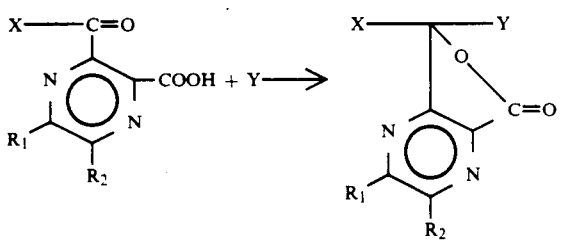

wherein X, Y $R_1$ and $R_2$ have the given meanings.

An alternative process for the compounds of the present invention, hereinafter referred to as process II, consists of the following series of reactions wherein $R_1$ and $R_2$ have the given meanings.

The first step in process II consists of reacting diaminomaleonirrile with the appropriate α-ketooaldehyde or αβ-diketone to produce a dinitrile.

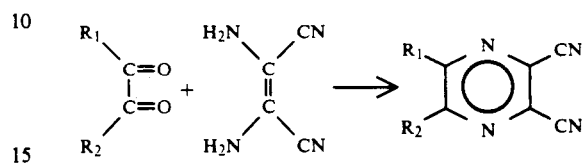

The resulting dinitrile is then hydrolyzed to the substituted pyrazine 2,3-dicarboxylic acid.

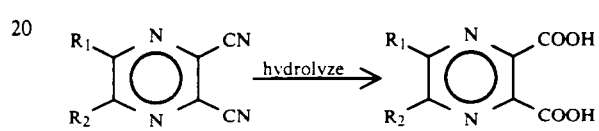

Once the proper substituted pyrazine 2,3-dicarboxylic acid is obtained, the remainder of the steps in process I are followed, resulting in the appropriate chromogenic compound.

The following is provided as a detailed example of the production of a chromogenic compound of the present invention by process I.

EXAMPLE 1

Preparation of 5,6-dimethylpyrazine-2,3-dicarboxylic acid.

A solution of 24 g. (0.152 mole) of 2,3-dimethylquinoxaline in 1150 ml. of water was heated to 80° C. Good stirring was maintained while 150 g. (0.95 mole) of potassium permanganate was added in approximately 4 g portions over a 2.5 hour period. The temperature was held at 80°-85° C. during this addition. The reaction mixture was heated one additional hour at 90° C.

The manganese dioxide was removed by filtration (hot) and washed several times with 25 ml. portions of hot water.

The filtrate was evaporated to approximately one half volume under reduced pressure. The aqueous solution was treated with 75 ml. of 37% hydrochloric acid. Evaporation was continued to a volume of 200 ml. On cooling there was obtained 23 g. (77%) of desired product, mp. 187°-188° C.

Preparation of 5,6-dimethylpyrazine-2,3-dicarboxylic anhydride.

A mixture of 23 g. (0.117 mole) of 5,6-dimethylpyrazine-2,3-dicarboxylic acic and 80 ml. of acetic anhydride was heated for 5 hours at 90° C. The hot reaction mixture was filtered to remove some insoluble material.

The filtrate was evaporated under reduced pressure until precipitation started. The mixture was cooled, filtered and the solid washed with hexane. The yield to anhydride was 11.8 g. (61%), mp. 170°-171° C. Infrared showed anhydride carbonyl peaks at 1792 nm. and 1734 nm. No free acid peaks were present.

Preparation of (1-ethyl-2-methylindol-3-yl)(2-carboxyl-5,6-dimethylpyrazin-3-yl)ketone.

To a solution of 12.72 g. (0.08 mole) of 1-ethyl 2 methylindole in 90 ml. of toluene and 10 ml. of acetonitrile was added 11.8 g. (0.073 mole) of 5,6-dimethylpyrazine-2,3-dicarboxylic anhydride. The reaction was run 20 hours at 55° C.

The reaction solution was added to 300 ml. of water containing 4 g of sodium hydroxide. The toluene and aqueous layers were separated and the aqueous layer extracted twice more with 50 ml. portions of toluene.

The aqueous layer, on acidification with hydrochloric acid, yielded 14.98 g. (67%) of the desired keto-acid, mp. 142°-144° C. Infrared showed acid carbonyl at 1742 nm. and ketone carbonyl at 1626 nm. The mass spectrum of the keto-acio (mw 337) gave a parent peak of m/z, 337 and base peak of m/z, 292 (tacile loss of $CO_2H$)

Preparation of 5-(1-ethyl-2-methylindol-3-yl)-5-(4-diethylamino-2-ethoxyphenyl)-5,7-dihydrofuro[3,4-b]-2,3-dimethylpyrizin-7-one.

A mixture of 4.04 g. (0.012 mole) of (1-ethyl-2-methylindol-3-yl)(2-carboxy-5,6-dimethylpyrazin-3-yl)ketone, 2.31 g. (0.012 mole) of N,N-diethylamino-m-phenetidine and 25 ml. of acetic anhydride was heated three hours at 55°-60° C.

The reaction solution was slowly dropped into 200 ml. of water containig 22.5 g. of sodium hydroxice. After one hour stirring at 45° C. the solid was filtered, washed well with water and finally with hexane.

The crude product (5.3 g.) was purified by two treatments, one with 15 ml. and one with 10 ml. of methyl alcohol. In each treatment the slurry was heated to reflux, cooled and filtered. The yield of purified color former was 4.17 g. (68%), mp. 179°-180° C. The infrared lactone carbonyl peak was found at 1772 nm. The mass spectrum of the dye (mw 512) gave a parent peak of m/z, 512.

The chromogenic compounds of this invention are eligible for use in pressure-sensitive and thermally-sensitive mark-forming systems. Pressure-sensitive mark-forming systems provide a marking system of disposing on and/or within sheet support material unreacted mark-forming components and a liquid solvent in which one or both of the mark-forming components is soluble, said liquid solvent being present in such form that it is maintained isolated by a pressure-rupturable barrier from at least one of the mark-forming components until application of pressure causes a breach of the barrier in the area delineated by the pressure pattern. The mark-forming components are thereby brought into reactive contact, producing a distinctive mark. In such pressure-sensitive mark-forming systems the chromogenic compounds of this invention will typically be used in combination with other chromogenic compounds which individually produce marks of different colors so that in combination the reaction between the chromogenic materials and the acidic color developer material produce a mark having a black perceived image. This black mark-forming system constitutes a specific subsidiary feature of the invention.

The pressure-rupturable barrier, which maintains the mark-forming components in isolation, preferably comprises microcapsules containing liquid solvent solution. The microencapsulation process utilized can be chosen from the many known in the art. Well known methods are disclosed in U.S. Pat. Nos. 2,800,457; 3,041,29; 3,533,958, 3,755,190; 4,001,140 and 4,100,103. Any of these and other methods are suitable for encapsulationg the liquid solvent containing the chromogenic compounds of this invention.

The method of marking comprises providing a chromogenic compound of the present invention and bringing such chromogenic compound into reactive contact, in areas where marking is desired, with an acidic color developer material to produce a colored form of the chromogenic compound.

The acidic materials can be any compound within the definition of a Lewis acid, i.e. an electron acceptor. These material include clay substances such as attapulgite, bentonite and montmorillonite and treated clays such as silton clay as disclosed in U.S. Pat. Nos. 3,622,364 and 3,753,761, materials such as silica gel, talc, feldspar, magnesium trisilicate, pyrophyllite, zinc sulfate, zinc sulfide, calcium sulfate, calcium citrate, calcium phosphate, calcium fluoride and barium sulfate, aromatic carboxylic acids such as salicyclic acid, derivatives of aromatic carboxylic acids and metal salts thereof as disclosed in U.S. Pat. No. 4,022,936, acidic polymeric material such as phenol-formaldehyde polymers, phenol-acetylene polymers, maleic acid-rosin resins, partially or wholly hydrolyzed styrene-maleic anhydride copolymers and ethylene-maleic anhydride copolymers, carboxy polymethylene and wholly or partially hydrolyzed vinyl methyl ether maleic anhydride copolymers and mixtures thereof as disclosed in U.S. Pat. No. 3,672,935, biphenols as disclosed in U.S. Pat. No 3,244,550 and addition products of a phenol and a diolefinic alkylated or alkenylated cyclic hydrocarbon as disclosed in U.S. Pat. No. 4,573,063

Particularly useful as acidic color developer substances are the metal-modified phenolic resins. Record sheet material coated with such resins is disclosed in U.S. Patent No. 3,732,120. An example of the compositions which can be coated onto the surface of a sheet to react with the chromogenic compounds of this invention is listed below in Table 1.

TABLE 1

| Coating Composition | Percent by Weight |
|---|---|
| Zinc-modified phenolic polymer | 13.6 |
| Paper coating kaolin | 67.9 |
| Calcium carbonate | 6.0 |
| Styrene-butadiene latex | 6.0 |
| Etherified corn starch | 6.5 |

Thermally-sensitive mark-forming systems are well known in the art and are described in many patents, for example U.S. Pat. Nos. 3,539,375; 3,674,535, 3,746,675;

4,151,748; 4,181,771 and 4,246,318. In these systems basic chromogenic material and acidic color developer material are contained in a coating on a substrate which, when heated to a suitable temperature, melts or softens to permit said materials to react, thereby producing a colored mark.

The following examples are given merely as illustrative of the present invention and are not to be considered as limiting.

The intermediates required for the preparation of the novel chromogenic compounds of this invention are classes of compounds readily obtained by procedures well known in the prior art.

Using either process I or process II, supra, the Examples represented by the structures listed in Table 2, based upon the following general formula, were prepared by the corresponding process listed.

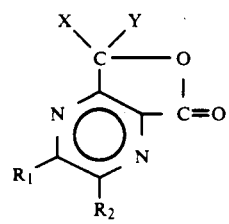

TABLE 2

| Ex. No. | X | Y | $R_1$ | $R_2$ | Process |
|---|---|---|---|---|---|
| 1. | (C$_2$H$_5$)$_2$N—C$_6$H$_3$(OC$_2$H$_5$)— | 1-ethyl-2-methyl-indol-3-yl | —CH$_3$ | —CH$_3$ | I |
| 2. | (C$_2$H$_5$)$_2$N—C$_6$H$_3$(OC$_2$H$_5$)— | 1-octyl-2-methyl-indol-3-yl | —CH$_3$ | —CH$_3$ | II |
| 3. | (C$_2$H$_5$)$_2$N—C$_6$H$_3$(OC$_2$H$_5$)— | C$_6$H$_5$(C$_2$H$_5$)N—C$_6$H$_3$(OC$_2$H$_5$)— | —CH$_3$ | —CH$_3$ | II |
| 4. | (C$_2$H$_5$)$_2$N—C$_6$H$_3$(OC$_2$H$_5$)— | (C$_2$H$_5$)$_2$N—C$_6$H$_3$(OC$_2$H$_5$)— | —CH$_3$ | —CH$_3$ | II |
| 5. | (C$_2$H$_5$)$_2$N—C$_6$H$_3$(OC$_8$H$_{17}$)— | 1-ethyl-2-methyl-indol-3-yl | —CH$_3$ | —CH$_3$ | II |
| 6. | C$_6$H$_5$(C$_2$H$_5$)N—C$_6$H$_3$(OC$_2$H$_5$)— | 1-ethyl-2-methyl-indol-3-yl | —CH$_3$ | —CH$_3$ | I & II |
| 7. | C$_6$H$_5$(C$_4$H$_9$)N—C$_6$H$_3$(OC$_2$H$_5$)— | 1-ethyl-2-methyl-indol-3-yl | —CH$_3$ | —CH$_3$ | II |

TABLE 2-continued
| Ex. No. | X | Y | R₁ | R₂ | Process |
|---|---|---|---|---|---|
| 8. | 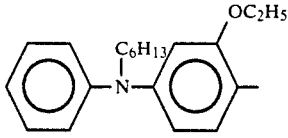 | 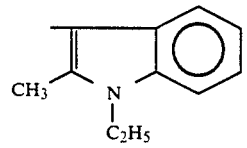 | —CH₃ | —CH₃ | II |
| 9. | 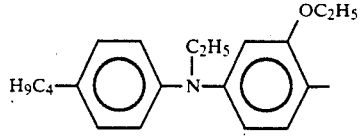 | 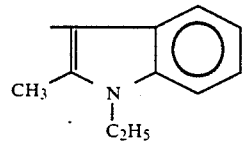 | —CH₃ | —CH₃ | I |
| 10. | 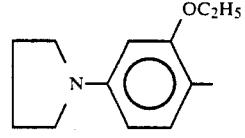 | 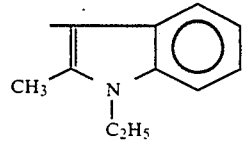 | —CH₃ | —CH₃ | I |
| 11. | 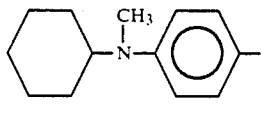 | 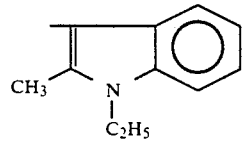 | —CH₃ | —CH₃ | I |
| 12. | 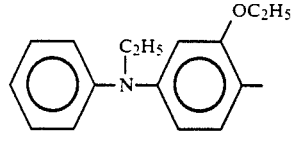 | 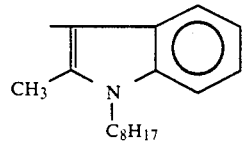 | —CH₃ | —CH₃ | II |
| 13. | 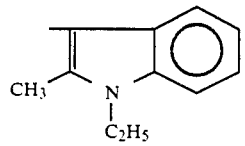 | 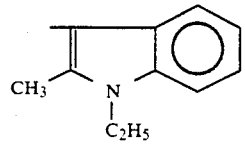 | —CH₃ | —CH₃ | II |
| 14. | 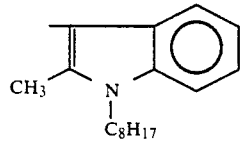 | 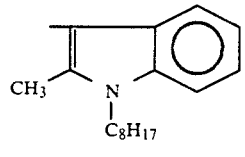 | —CH₃ | —CH₃ | II |
| 15. | 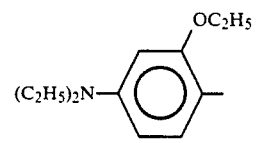 | 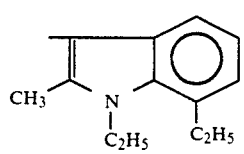 | —CH₃ | —CH₃ | II |
| 16. | 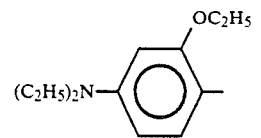 | 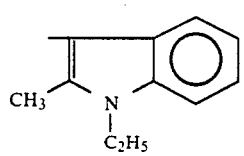 | —CH₃ | —C₂H₅ | II |
| 17. | 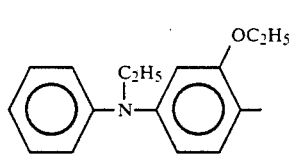 | 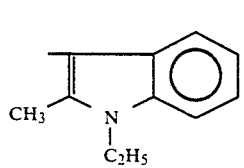 | —CH₃ | —C₂H₅ | II |

TABLE 2-continued

| Ex. No. | X | Y | R₁ | R₂ | Process |
|---------|---|---|-----|-----|---------|
| 18. | phenyl-N(C₂H₅)-(3-OC₂H₅-4-CH₃-phenyl) | 2-methyl-1-cyclohexyl-indole | $-CH_3$ | $-CH_3$ | I |
| 19. | 2-methyl-1-ethyl-indole | 2-methyl-1-ethyl-indole | $-CH_3$ | $-C_2H_5$ | II |
| 20. | (C₂H₅)₂N-(3-OC₂H₅-4-CH₃-phenyl) | 2-methyl-1-ethyl-indole | $-C_2H_5$ | $-C_2H_5$ | II |
| 21. | phenyl-N(C₂H₅)-(3-OC₂H₅-4-CH₃-phenyl) | 2-methyl-1-ethyl-indole | $-C_2H_5$ | $-C_2H_5$ | II |
| 22. | (C₂H₅)₂N-(3-OC₂H₅-4-CH₃-phenyl) | 2-methyl-1-ethyl-indole | $-H$ | phenyl | II |
| 23. | (4-H₉C₄-phenyl)-N(C₂H₅)-(3-OC₂H₅-4-CH₃-phenyl) | 2-methyl-1-ethyl-indole | $-H$ | phenyl | II |
| 24. | phenyl-N(C₄H₉)-(3-OC₂H₅-4-CH₃-phenyl) | 2-methyl-1-ethyl-indole | $-H$ | phenyl | II |
| 25. | (C₂H₅)₂N-(3-OC₂H₅-4-CH₃-phenyl) | 2-methyl-1-ethyl-indole | $-H$ | $-CH_3$ | II |
| 26. | (C₂H₅)₂N-(3-OC₂H₅-4-CH₃-phenyl) | 2-methyl-1-ethyl-indole | $-CH_3$ | phenyl | II |

TABLE 2-continued

| Ex. No. | X | Y | $R_1$ | $R_2$ | Process |
| --- | --- | --- | --- | --- | --- |
| 27. | [structure: phenyl-N(C2H5)-phenyl with OC2H5 and CH3 substituents] | [structure: indole with CH3, N-C2H5] | —H | CH3 | II |
| Reference Compound | [structure: (C2H5)2N-phenyl with OC2H5 and CH3 substituents] | [structure: indole with CH3, N-C2H5] | —H | —H | I |

The compounds of Examples 16, 17, 19, 22, 23, 24, 25, 26 and 27 were actually mixtures of the isomers (1) wherein the substituents for $R_1$ and $R_2$ are as indicated and (2) wherein the substituents for $R_1$ and $R_2$ are reversed from what is indicated.

In Table 3 are listed, for each Example of Table 2, the respective melting point, molecular weight as determined by mass spectrometry, color developed when applied to a metal-modified phenolic resin color developer composition as disclosed in Table 1, amount of color developed in a tesr designed to simulate coloration on base paper and amount of color developed in a test designed to simulate microencapsultion conditions.

The test designed to simulate coloration on base paper consisted of the preparation of a $2.06 \times 10^{-2}$ molar solution of each Example compound in toluene, the application of a 0.02 ml. portion of the resulting solution to Whatman #1 filter paper, and, after evaporation of the toluene, the measurement of the amount of color development on the filter paper reported as the ratio of the reflectance of the colored area to that background reflectance of the filter paper (I/Io). The greater the numerical value of this ratio, the lower the quantity of color produced.

The test designed to simulate color development under microencapsulation conditions consisted of mixing and agitating a 2.0 ml. portion of a $2.06 \times 10^{-2}$ molar solution of each Example compound in toluene with 2.0 ml of water. The water and toluene layers were separated and the absorbance of the water layer was measured at respective visible absorption maximum of the Example compound.

TABLE 3

| Example No. | Melting Point | Molecular Weight | Color | Base Paper Color | Microencapsulation Color |
| --- | --- | --- | --- | --- | --- |
| 1 | 179–180° C. | 512 | blue | 0.72 | 1.23 |
| 2 | 78–82° C. | 596 | blue | 0.78 | 0.06 |
| 3 | 182–183° C. | 594 | blue-green | 0.94 | 0.04 |
| 4 | 145–146° C. | 546 | blue-green | 0.85 | 0.23 |
| 5 | 109–110° C. | 596 | blue | 0.71 | 0.10 |
| 6 | 156–158° C. | 560 | blue | 0.92 | 0.27 |
| 7 | 85–88° C. | 588 | blue | 0.94 | 0.05 |
| 8 | 171.5–173° C. | 616 | blue | 0.95 | 0.02 |
| 9 | 155–158° C. | 616 | blue | 0.92 | 0.02 |
| 10 | 210–212° C. | 510 | blue | 0.72 | 1.11 |
| 11 | 98–100° C. | 508 | blue | 0.94 | 0.18 |
| 12 | 65–68° C. | 644 | blue | 0.78 | 0.06 |
| 13 | 208–210° C. | 478 | red | 0.78 | 3.13 |
| 14 | 112–113° C. | 646 | red | 0.79 | 0.10 |
| 15 | 112–114° C. | 540 | blue | 0.76 | 0.59 |
| 16 | 174–177° C. | 526 | blue | 0.76 | 0.29 |
| 17 | 135–138° C. | 574 | blue | 0.91 | 0.18 |
| 18 | 197–198° C. | 614 | blue | 0.89 | 0.02 |
| 19 | 104–107° C. | 492 | red | 0.69 | 1.53 |
| 20 | 167–168.5° C. | 540 | blue | 0.64 | 0.29 |
| 21 | 165–168° C. | 588 | blue | 0.86 | <0.02 |
| 22 | 171–174° C. | 560 | blue | 0.59 | <0.02 |
| 23 | 92–95° C. | 664 | blue | 0.84 | <0.02 |
| 24 | 118–123° C. | 636 | blue | 0.88 | <0.02 |
| 25 | 163–165° C. | 498 | blue | 0.58 | 1.48 |
| 26 | 118–122° C. | 574 | blue | 0.54 | 0.07 |
| 27 | 84–87° C. | 546 | blue | 0.80 | 0.07 |
| Reference Compound | 175–176° C. | 484 | blue | 0.68 | 1.89 |

From the data on Table 3 it is readily apparent that the chromogenic compounds of the present invention possess unexpected improved resistance to base stock coloration and/or improved resistance to coloration during microencapsulation compared to compounds disclosed in the prior art.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A compound represented by the formula:

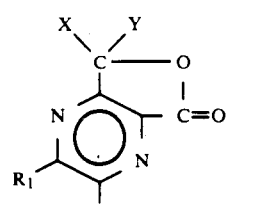

wherein X is

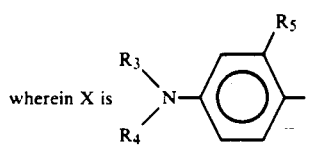

wherein Y is

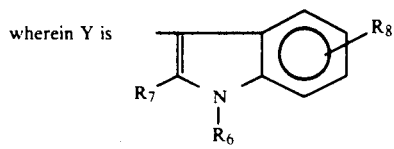

wherein $R_5$ is hydrogen or lower alkoxy;
wherein $R_6$ is ethyl;
wherein $R_7$ is methyl;
wherein $R_8$ is hydrogen;
wherein $R_3$ is $C_1$-$C_8$ alkyl;
wherein $R_4$ is phenyl or phenyl substituted by lower alkyl;
wherein $R_1$ and $R_2$, are each independent of the other, lower alkyl.

2. A compound represented by the formula:

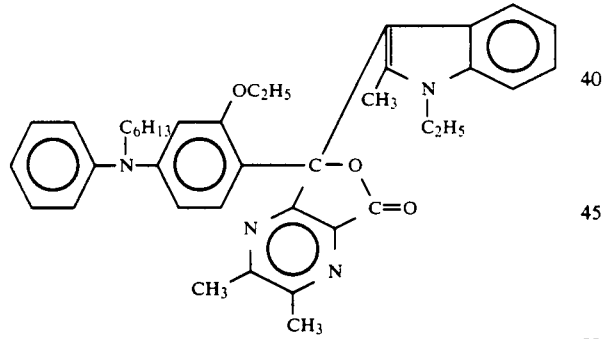

3. A compound represented by the formula:

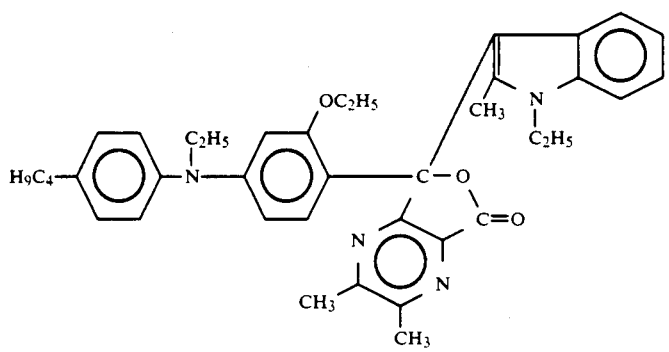

4. A compound represented by the formula:

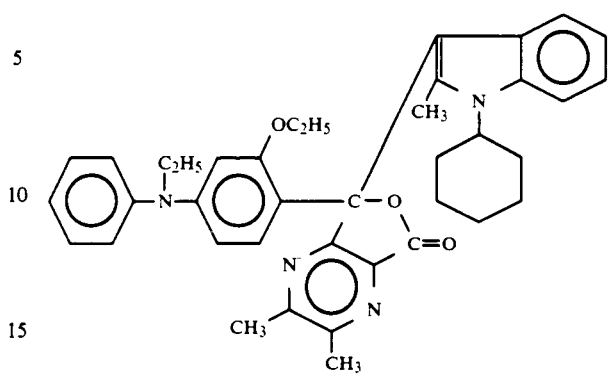

5. A compound represented by the formula:

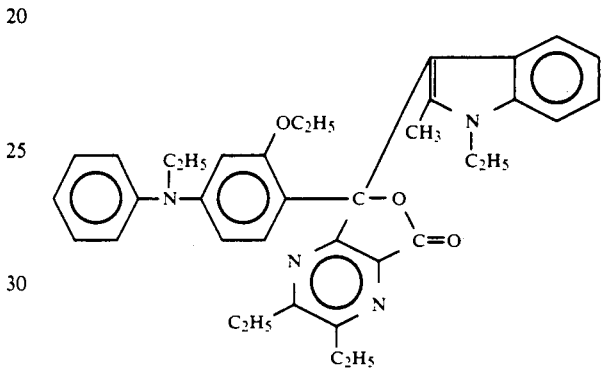

6. A compound represented by the formula:

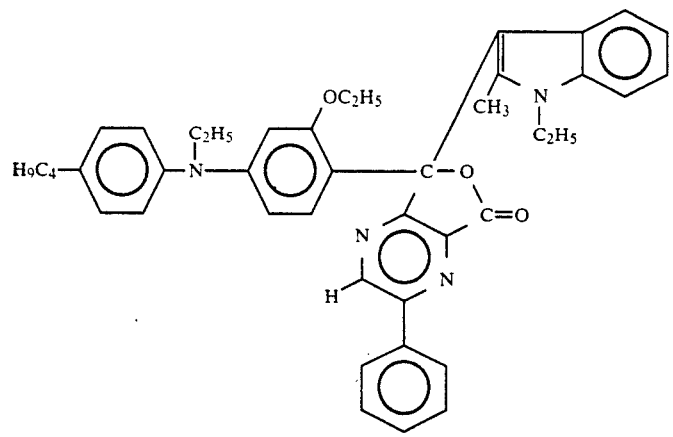

7. A compound represented by the formula:

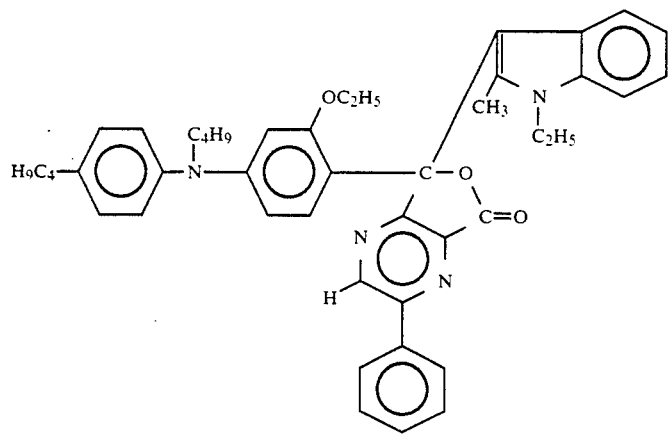

8. A compound represented by the formula:

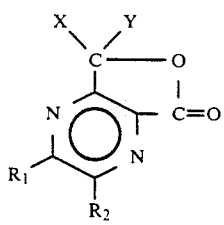

wherein X is

[structure showing N with R3, R4, R5 substituents on phenyl]

wherein Y is

[indole structure with R6, R7, R8]

wherein $R_5$ is hydrogen or lower alkoxy;
wherein $R_6$ is ethyl;
wherein $R_7$ is methyl;
wherein $R_8$ is hydrogen;
$R_3$ is $C_1$–$C_8$ alkyl;
wherein $R_4$ is cyclohexyl;
wherein $R_1$ and $R_2$, are each independent of the other, lower

* * * * *